(12) United States Patent
Saul

(10) Patent No.: US 9,135,404 B2
(45) Date of Patent: Sep. 15, 2015

(54) METHOD FOR MONITORING AN INDIVIDUAL'S FAT METABOLISM STATE

(76) Inventor: Indrek Saul, Harjumaa (EE)

( * ) Notice: Subject to any disclaimer, the term of this patent is extended or adjusted under 35 U.S.C. 154(b) by 194 days.

(21) Appl. No.: 13/229,096

(22) Filed: Sep. 9, 2011

(65) Prior Publication Data

US 2012/0065895 A1 Mar. 15, 2012

Related U.S. Application Data

(63) Continuation-in-part of application No. PCT/EE2010/000006, filed on Mar. 8, 2010.

(51) Int. Cl.
*G01N 33/48* (2006.01)
*G06F 19/00* (2011.01)

(52) U.S. Cl.
CPC .................. *G06F 19/3475* (2013.01)

(58) Field of Classification Search
CPC ................................... G06F 19/3475
USPC .......................................... 702/19
See application file for complete search history.

(56) References Cited

U.S. PATENT DOCUMENTS

| | | | |
|---|---|---|---|
| 6,354,996 B1 | 3/2002 | Drinan et al. | |
| 6,506,152 B1 | 1/2003 | Lackey et al. | |
| 6,719,667 B2 | 4/2004 | Wong et al. | |
| 7,285,090 B2 | 10/2007 | Stivoric et al. | |
| 2002/0193702 A1 | 12/2002 | Yamazaki et al. | |
| 2003/0223905 A1 | 12/2003 | Moerman | |
| 2006/0253010 A1 | 11/2006 | Brady et al. | |
| 2008/0004501 A1* | 1/2008 | Gavrilov | 600/300 |
| 2009/0112069 A1* | 4/2009 | Kanamori et al. | 600/300 |
| 2009/0270728 A1* | 10/2009 | Da Silva et al. | 600/437 |

FOREIGN PATENT DOCUMENTS

| | | |
|---|---|---|
| EP | 1576923 A1 | 9/2005 |
| EP | 1707118 A2 | 10/2006 |
| JP | 2000-166890 | 6/2000 |
| WO | 2009131664 A2 | 10/2009 |

OTHER PUBLICATIONS

PCT Search Report dated May 27, 2010 of Patent Application No. PCT/EE2010/000006 filed Mar. 8, 2010, 3 pages.

* cited by examiner

*Primary Examiner* — Jerry Lin
(74) *Attorney, Agent, or Firm* — Maine Cernota & Rardin

(57) ABSTRACT

Method of monitoring energy consumption of an individual in an information system, comprised of periodically determining the energy balance of the individual by measuring body fat percentages (or body fat mass) at least at three consecutive moments of time and calculating change of body fat percentages (body fat mass) from two consecutive moments of time, and calculating the trends of the individual's energy balance from the changes of body fat percentages (body fat mass) and determining from the trend whether the individual is in the stage of burning or accumulating fat. The information system automatically generates recommendations for controlling energy balance based on the trends of changes of the energy balance.

8 Claims, 3 Drawing Sheets

METHOD FOR MONITORING AN INDIVIDUAL'S FAT METABOLISM STATE

RELATED APPLICATIONS

This application is a continuation-in-part of PCT Appl. No PCT/EE2010/000006—filing date Mar. 8, 2010 which is herein incorporated by reference for all purposes.

TECHNICAL FIELD

This invention belongs among the methods and devices used for monitoring the fat metabolism state of an individual.

BACKGROUND ART

Various methods and devices for monitoring human energy consumption are known in practice. Diet and physical effort planning decisions are made for the individual based on the monitoring results.

U.S. Pat. No. 6,719,667 describes a belt training device equipped with electronic scales that monitor the change of the individual's weight, and the device calculates the amount of energy spent using the installed software. The results are displayed on the screen.

U.S. Pat. No. 7,285,090 describes a device monitoring the ratio of the energy spent and assimilated by an individual using sensors attached to the individual's body. The information is wirelessly transmitted from the sensors to an electronic device where the information is processed by the software installed in the device. Information on the food consumed is entered in the device and the amount of assimilated energy is determined based on this information. The ratio of spent and assimilated energy is determined by processing the total information entered.

Patent application No. US20060253010 describes a sports watch that enables measuring of the energy spent by the individual by using an indirect method, based mainly on the heart rate, weight and age of the individual.

U.S. Pat. No. 6,506,152 describes a method that first calculates the predicted body fat percentage change on the basis of calories consumed from food and calories spent, and after that calculates the energy balance correction factor based on the actual and predicted change of body fat percentage.

Patent application No. US20020193702 describes calculation of the body fat percentage based on a bioimpedance measurement and the individual's individual data, setting the desired body fat percentage as a goal, determining the amount of calories to be spent based on the actual body fat percentage and the body fat percentage set as the goal, and determining the exercising activity required to achieve it.

The drawback of all the above mentioned solutions is the fact that the energy consumption of an individual, and the loss of body fat mass or percentage resulting from that, is determined indirectly based on the amount of energy (calories) consumed and spent, by applying the so-called Harris-Benedict formula, and the results obtained may differ from the actual results. These so-called calorimetric methods also require monitoring of the amount of energy (calories) consumed and spent.

Scales capable of determining the body fat mass and percentage are known, indicating the change of body fat mass and percentage based on two consecutive measurements (e.g. Body Signal scales from the TEFAL brand). The scales can easily give faulty results on the basis of two consecutive measurements—a positive result (decrease of body fat amount) is indicated based on a single change, but at the same time the trend of body fat accumulation continues.

SUMMARY OF THE INVENTION

The purpose of this invention is to provide a method for monitoring fat metabolism state (direction) of an individual, which includes determination of individual's body fat mass (or its relative change) performed at more than two consecutive moments of time.

To achieve the purpose of this invention the individual's fat metabolism state is determined by the information system based on changes of body fat mass. An information system and software are used to determine whether the individual is in a fat accumulation or fat burning stage, and based on these data recommendations for controlling the individual's fat metabolism state are automatically generated by the information system.

EXAMPLE OF THE EMBODIMENT OF THE INVENTION

Figure 1:
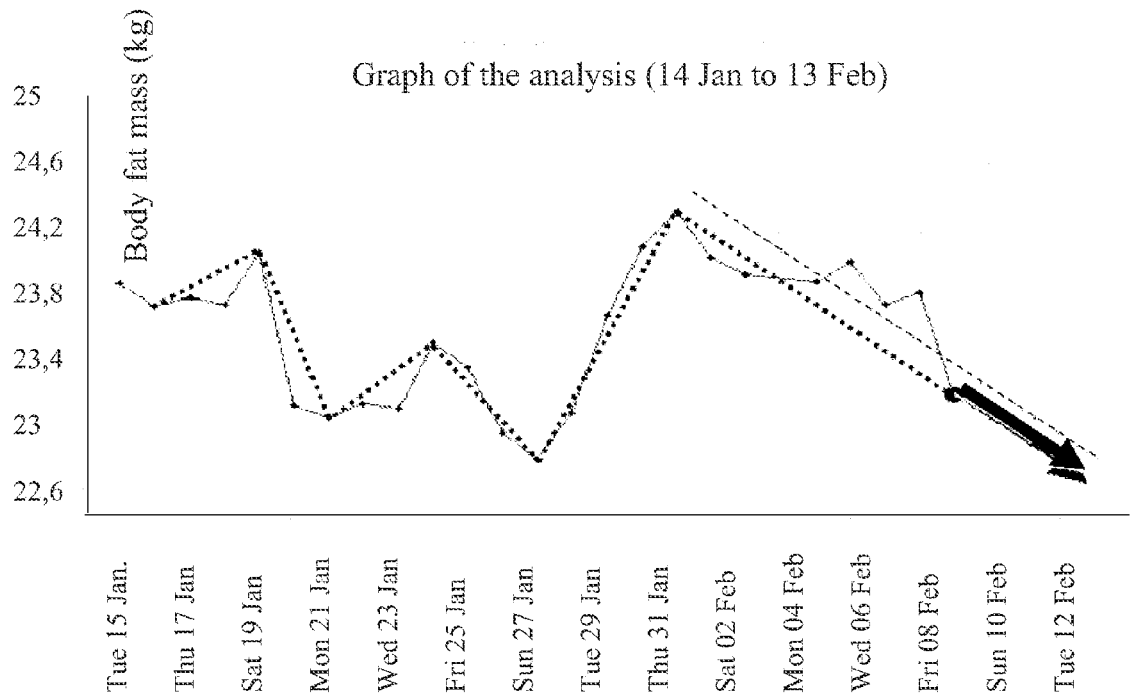
FIG. 1 depicts a chart of body fat mass changes (continuous line) with the trend of the fat mass change (dotted line).

FIG. 1 depicts a chart of body fat mass changes (continuous line) with the trend of the fat mass change (dotted line). As can be seen, several phases of fat accumulation and fat burning follow each other. For successful weight control it is important to determine whether the body is in fat accumulation state or fat consuming (fat burning) state. It has been noticed that turning the fat accumulation state into fat burning state takes much more effort than steadily maintaining fat burning state.

According to one embodiment example of the invention the individual's body fat mass and its changes are determined periodically as follows.

The individual's body fat mass from the first moment of time is entered into the information system. After that the body fat mass from the subsequent moment of time (for example, after one day) is entered into the information system. The body fat mass change is calculated based on two consecutive body fat mass values. Body fat mass from consecutive moments of time (daily, every two days, etc.) are entered in the system, and consecutive body fat mass changes are calculated based on body fat mass measured at two consecutive moments of time, and body fat mass trends are calculated in turn, based on consecutive body fat mass changes. Changes and trends are visualised using a suitable method, e.g. graphically.

The body fat mass is determined with the help of any method known from the state of the art, for example the liquid method or bioimpedance method, using, e.g. scales equipped with the corresponding function (e.g. TEFAL Body Signal). As the changes of body fat mass and not its absolute value are essential for this method, the occurrence of a relatively large absolute error when using the bioimpedance method to determine body fat mass is not important assuming the random error is sufficiently small.

In addition to the individual's body fat mass other data are also entered in the information system, and based on these data individual weight control recommendations are offered, for example body weight, the individual's sex, date of birth, and height, as well as the description of the individual's behaviour and exercising habits, and the individual's goals and deadlines for achieving the change of body weight (and body fat percentage), and also the data pertaining to the individual's physiological and emotional condition.

The method comprises determining of the energy consumption trend based on several consecutive body fat mass changes (see FIG. 1). According to one version the linear trend is determined.

Figure 3:
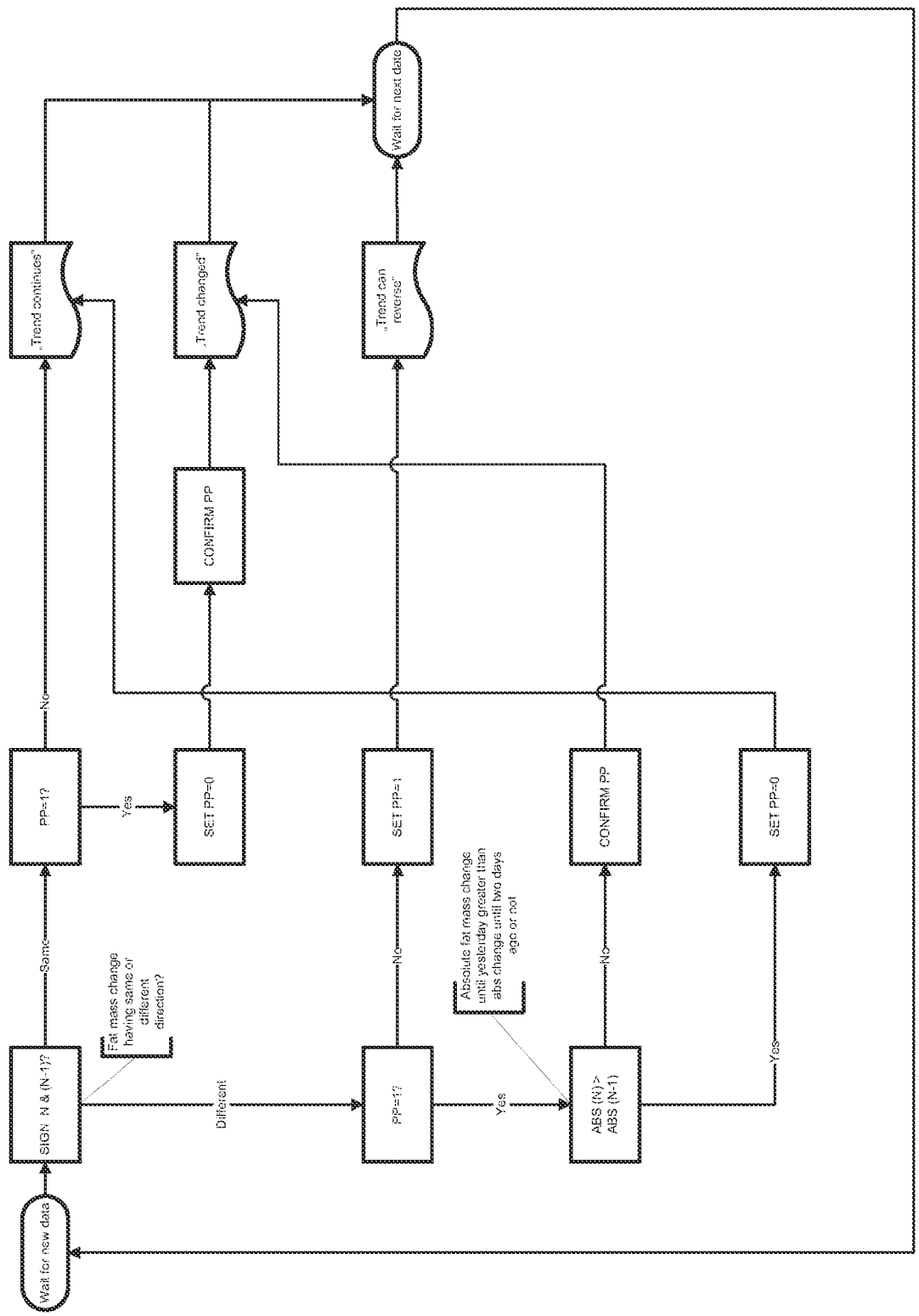
FIG. 3 depicts a flow chart according to one embodiment of the invention

According to one method as shown on FIG. 3, the energy consumption trend and trend change are determined based on the consecutive changes in individual's body fat mass. Preferably, the consecutive changes of the body fat are determined on consecutive days, at the same time of the day, on same conditions. The body fat mass trend and trend changes are determined in following steps.

A) A latest body fat change on day N is compared with previous body fat change on day N−1;

A1) if the signs of both changes (day N, day N−1) are the same (i.e., in both days the body fat mass was either decreasing or increasing), trend on day N continues in the same direction as on day N−1 and algorithm will start over the next day (N+1) when subsequent body fat mass (or change) data is received by the system A2) if the signs of changes on days N and N−1 are not the same, there could be a trend reversing point on day N−1 (potential trend reversing point, PTRP) as determined by the following steps:

B. For confirmation of the PTRP as an actual trend reversing point (TRP), and correspondingly, confirming the trend change on day N−1, the change N+1 following the change, is considered.

B1) If the sign of the change on day N+1 coincides with the change on day N, then there was an actual trend reversing point TRP at day N and the trend has reversed (changed direction) and the algorithm will start over on the next day.

B2) If the sign of the change on day N+1 differs from the change on day N, and

C1) if its absolute value is greater (i.e., |change on day N+1|>|change on day N|, the PTRP at time moment N is not actual trend reversing point, and the existing trend continues. Algorithm will start over on the next day.

C2) if its absolute value is smaller, then there was an actual trend reversal point at time moment N.

According to the second method the fat metabolism state are determined based on the consecutive changes of the body fat mass. System will continuously monitor the daily changes in the fat mass. When in continous daily usage, system has in memory the daily fat mass amounts. From that the daily fat mass changes have been previously calculated and stored in memory. When todays fat mass is entered into the system, the system will calculate the change in the fat mass for the yesterday. System will perform logical test A—compare the direction of the change in the fat mass from day before yesterday until yesterday (the first change) with the direction of the change of the fat mass from yesterday until today (the second change). If A1) the directions of the change 1 and change 2 are the same, there is no changes in the direction of the trend and the underlying trend continues. If A2) the direction of the second change differs from the direction of the first change, today could be the starting point (potential trend reversing point—PTRP) of the opposite trend. Fat metabolism could reverse from "burning state", using the energy stored in the fat tissue into the "storing state", accumulating the excess of the energy balance into the fat tissue or vice versa. System will issue a corresponding warning message and recommendations to the individual. Compared with any known trend calculation methods this one is the fastest, allowing not just determining the trend of the fat metabolism, but issue a warning within 24 hours when the trend is about to change from "burning" to "storing".

The fat metabolism state of the following 24 hours are critical in either for reverting the existing trend or assuring the continuation of it. It is known, that it is considerably easier to maintain fat metabolism in "burning" state than reverting it from "storing" to "burning", Thus, this alghoritm provides dieter with unprecedent tool to maintain the fat metabolism in "burning" state and increasing the overall efficasy and effectiveness of weight control.

Next day the logical test B as described above is performed by the system.

After that the third change following the second change is considered. If the direction of the third change coincides with that of the second change the trend has reversed. If, however, the direction of the third change differs from that of the second change, and its absolute value is greater the point cannot be considered a potential reversing point, and the recent trend continues. If the direction of the third change differs from that of the second change but its absolute value is smaller, and the increase during the last day and the last but one day is less than the slope of the linearly interpolated trend line calculated on the basis of the previous reversing point then an opposite direction trend started from the previous potential reversing point, i.e. a new potential reversing point was created. In that case the fourth change following the third change is used to determine whether the point in question was a potential reversing point. If, however, the increase exceeds the slope of the trend, the recent trend continues.

Figure 2:
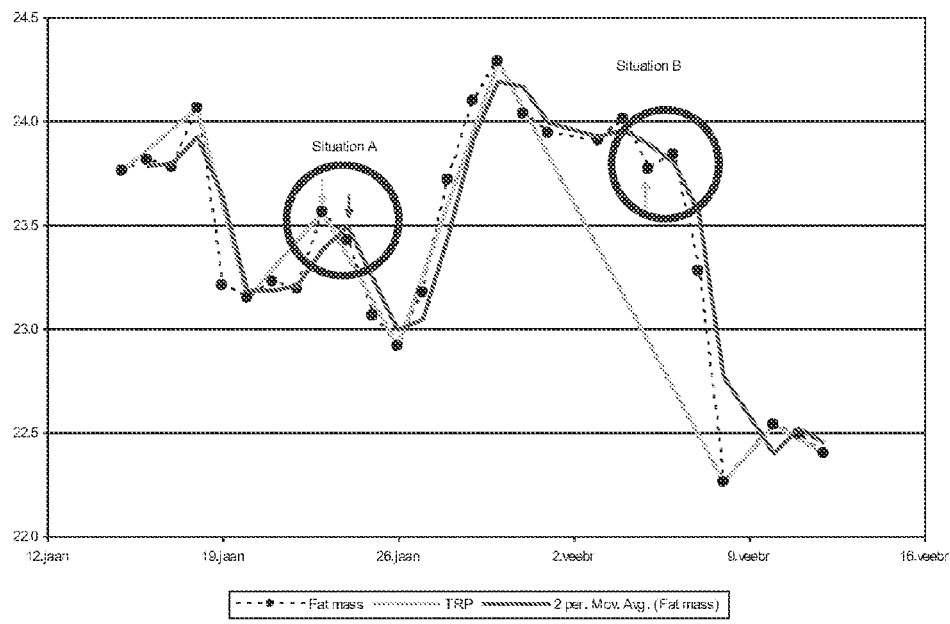
FIG. 2 depicts the invented method in comparison with 2 period moving average when applied for the same purpose as the invention.

Compared to known methods, the invented method is faster and more reliable as to the potential trend reversal points. As can be seen of FIG. 2, the invented method discovers trend reversal earlier (situation A) and recognises potential trend reversal points (situation B) as a threat to successful weight control even though when later appears that no actual trend reversal occurs.

Table 1 further describes how the method of FIG. 3 is applied, whereas the same set of data is used as shown on FIG. 1. Column "sign" shows whether the signs of changes on that date and on the previous date have the same sign, i.e., are in the same direction. Column "abs>" shows whether the absolute value of the change on that date is bigger than the day before. Column "PTRP" shows if a potential trend reversal point exists and on what date. "PP" shows the value of PP, which is first parameter for determining potential trend reversal point and which has values "0" and "1" that are changed as shown on flow chart on FIG. 3. Column SET PP shows whether the value of PP is changed on this date. Column "trend on this date" shows the conclusion as to the trend and possible change of trend based on data available on that date.

TABLE 1

| Date | Sign | Abs > ? | PTRP | PP | SET PP | Trend on this date |
|---|---|---|---|---|---|---|
| 15.01.10 | — | — | | 0 | 0 | — |
| 16.01.10 | — | — | | 0 | 0 | — |

TABLE 1-continued

| Date | Sign | Abs > ? | PTRP | SET PP | Trend on this date |
|---|---|---|---|---|---|
| 17.01.10 | diff | — | 16.01? | 1 | 0 | Possible reversal 16.01 |
| 18.01.10 | diff | no | 16.01 yes; | 1 | 1 | Changed (up since 16.01) |
| 19.01.10 | diff | yes | 17.01 not | 0 | 0 | Continues |
| 20.01.10 | diff | yes | 19.01? | 1 | 0 | Possible reversal 19.01 |
| 21.01.10 | same | no | 19.01 yes | 0 | 0 | Changed (down since 19.01) |
| 22.01.10 | diff | yes | 21.01? | 1 | 0 | Possible reversal 21.01 |
| 23.01.10 | diff | no | 21.01 yes | 1 | 1 | changed (up since 21.01) |
| 24.01.10 | diff | yes | | 0 | 0 | Continues |

Figure 4:
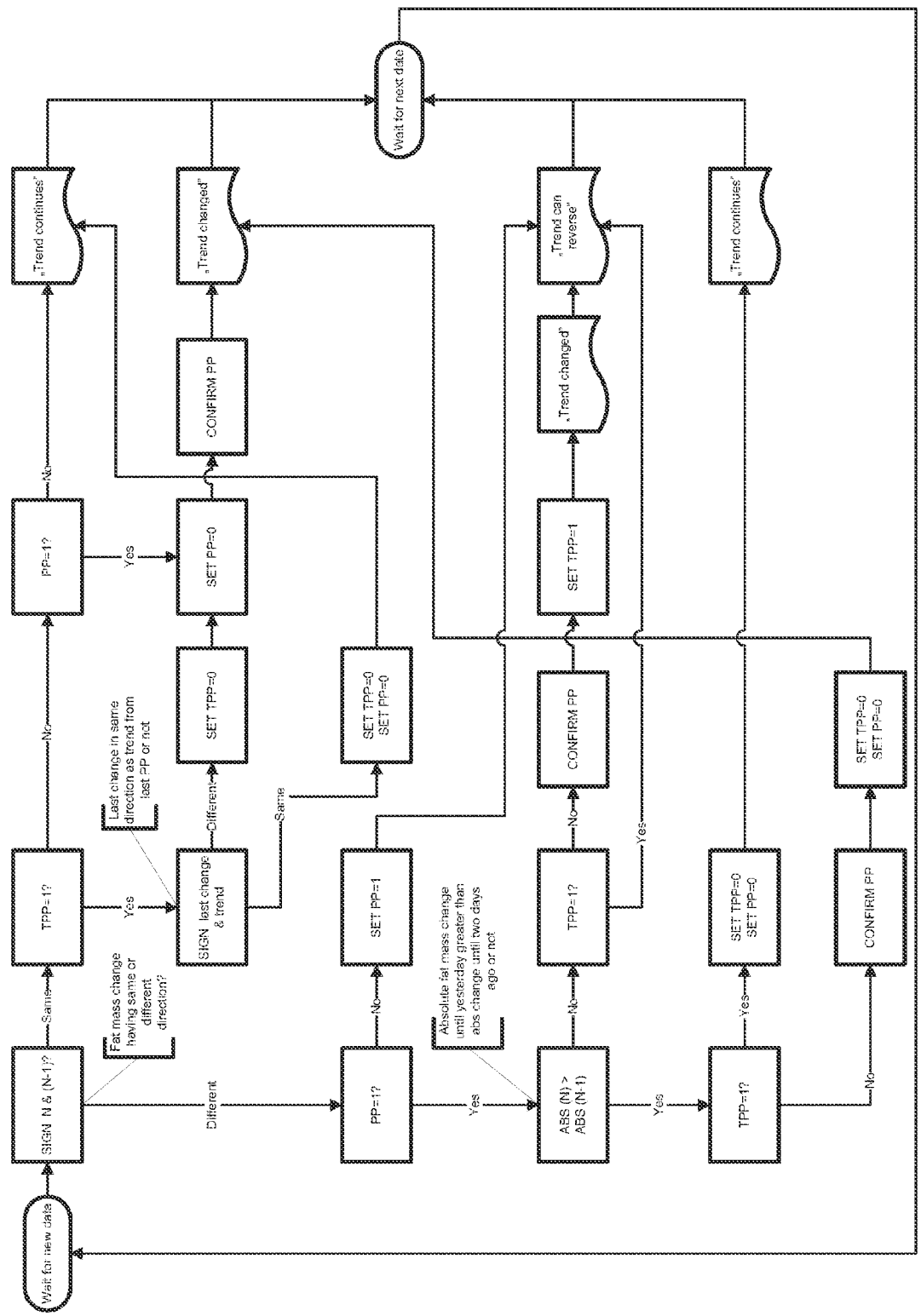
FIG. 4 depicts a flow chart according to another embodiment of the invention with more elaborate approach to potential trend reversal points.

FIG. 4 describes a flow chart of yet another embodiment of the invention. The abbreviations have the same meanings as above. TPP stands for second parameter for determining potential consecutive trend reversal point.

Table 2 further describes how the method of FIG. 4 is applied, whereas the same set of data is used as shown on FIG. 1. Columns "sign", "abs>", "PTRP", "SET PP" and "trend on this date" have the same meaning as in Table 1. Column "SET TPP" shows the value of parameter TPP on that date and the value of TPP is changed as shown on flow chart on FIG. 4.

TABLE 2

| Date | Sign | Abs > ? | PTRP | SET PP | SET TPP | Trend on this date |
|---|---|---|---|---|---|---|
| 15.01.10 | — | — | | 0 | 0 | — |
| 16.01.10 | — | — | | 0 | 0 | — |
| 17.01.10 | diff | — | 16.01? | 1 | 0 | Possible reversal 16.01 |
| 18.01.10 | diff | No | 16.01 yes; 17.01? | 1 | 1 | Changed (up since 16.01), possible reversal 17.01 |
| 19.01.10 | diff | Yes | 17.01 not | 0 | 0 | Continues |
| 20.01.10 | diff | Yes | 19.01? | 1 | 0 | Possible reversal 19.01 |
| 21.01.10 | same | No | 19.01 yes | 0 | 0 | changed (down since 19.01) |
| 22.01.10 | diff | Yes | 21.01? | 1 | 0 | Possible reversal 21.01 |
| 23.01.10 | diff | No | 21.01 yes, 22.01? | 1 | 1 | changed (up since 21.01) |
| 24.01.10 | diff | Yes | 22 not | 0 | 0 | Continues |

Important advantage is that not just the actual trend reversal points have value for weight control, but also the potential trend reversal points. This gives the individual an early warning if something tends to go in undesired direction.

In addition to that the factor analysis of the fat metabolism state could be performed to assess the impact of eating and exercising habits on the change of the energy balance.

In addition to the individual's body fat mass other data are also entered into the information system, and based on these data individual weight control recommendations can be generated. Such other data may include, for example body weight, sex, date of birth (age), height, as well as description of individual's behaviour, habits, goals and deadlines for achieving the results in weight control.

Descriptions of the individual's activities during the period are periodically entered in the information system, including data on the individual's weight control achievements and mistakes, and the individual's emotional condition. When the system identifies essential positive or negative changes, it gathers information on possible related activities, and periodically analyses the main causes of excess and deficiency. According to one version the individual's activities are entered in the information system with the same frequency as the body fat mass data (e.g. daily). According to another version the individual's activities are entered in the system associated with (especially) more extensive changes.

The individual's activities for the next period are planned by the information system and the individual, effectiveness of the measures applied is measured, possible weight control mistakes are forecast, measures to avoid the mistakes are planned, and recommendations for controlling the energy consumption are offered, based on the individual's goals, the changes of the energy balance, and the achievements and mistakes of energy consumption control.

According to one embodiment example of the invention the individual's body weight and body fat percentage are automatically transmitted from the corresponding measuring device (electronic scales) to the information system via a communications channel. The communications channel could be any of the known communications channels, e.g. LAN, Bluetooth, WiFi network, infrared connection, etc. The information system may reside in a personal computer, handheld computer, mobile phone either partially or in full, or be available via the Internet or intranet. The information system may reside in the measuring device partially or in full, e.g. in the scales.

The invention claimed is:

1. Method of monitoring an individual's fat metabolism state with an electronic scale using an information system residing in said electronic scale, the method comprising:
  regularly measuring by the electronic scale and storing in the information system a set of consecutive body fat data of the individual, said set of body fat data comprising the individual's body fat mass or body fat mass changes from one prescheduled consecutive time moment to the next prescheduled consecutive time moment, wherein said prescheduled consecutive time moments occur regularly from once a day to once in three days;
  calculating by the information system a trend of body fat mass change from said body fat mass changes for at least two consecutive time moments; and
  providing by the electronic scale the individual with a trend information each time the individual enters data into the information system, wherein said trend information is determined based on comparing the trend determined at the time moment the individual enters data into the information system, and at least the trend determined one prescheduled consecutive time moment earlier, and wherein said trend information contains a prediction whether the trend calculated for the next time moment will change, will be continued, or could either change or not depending on the individual's activities until said next time moment.

2. Method as in claim 1, wherein the prescheduled consecutive time moments occur once a day.

3. Method as in claim 2, wherein the trend information comprises information selected from a group consisting of trend direction, slope of the trend, confirmation of a continuing trend, occurrence of actual trend reversal at this moment of time, warning of a potential trend reversal, duration of a continuing trend, total gain or loss of the body fat mass or body mass during the trend, and warning of potential trend reversal in the future based on the trend.

4. Method as in claim 3, wherein the trend information comprises weight control progress related explanations for the individual to understand the trend information.

5. Method as in claim 4, wherein the trend information comprises providing the individual with weight control related recommendations.

6. Method as in claim 5, comprising receiving from the individual weight control related information and automatically making weight control related recommendations based on said individual weight control related information and the trend information.

7. Method as in claim 1, comprising providing the individual with body fat mass change related motivational messages to assist the individual to affect the trend according to a body fat change plan of the individual.

8. Method as in claim 7, comprising warning to the individual if the trend is about to change.

* * * * *